US00PP31521P2

(12) United States Plant Patent
de Groot

(10) Patent No.: US PP31,521 P2
(45) Date of Patent: Mar. 10, 2020

(54) ***ROSA* PLANT NAMED 'RUIRD0037A'**

(50) Latin Name: *Rosa hybrida*
Varietal Denomination: RUIRD0037A

(71) Applicant: Hendrikus de Groot, Amstelveen (NL)

(72) Inventor: Hendrikus de Groot, Amstelveen (NL)

(73) Assignee: De Ruiter Intellectual Property BV (NL)

( * ) Notice: Subject to any disclaimer, the term of this patent is extended or adjusted under 35 U.S.C. 154(b) by 0 days.

(21) Appl. No.: 16/350,980

(22) Filed: Feb. 7, 2019

(51) Int. Cl.
*A01H 5/02* (2018.01)
*A01H 6/74* (2018.01)

(52) U.S. Cl.
USPC ..... Plt./145
CPC ..... *A01H 6/74* (2018.05)

(58) Field of Classification Search
USPC ..... Plt./145
CPC ..... A01H 5/0222
See application file for complete search history.

*Primary Examiner* — Kent L Bell
(74) *Attorney, Agent, or Firm* — Cassandra Bright

(57) ABSTRACT

A new and distinct hybrid *Rosa* cultivar named 'RUIRD0037A' is disclosed, characterized by large, yellow flowers with a sweet fragrance. Plants are upright, and exhibit good resistance to blackspot diseases. The new variety is a *Rosa*, normally produced as an outdoor garden or container plant.

2 Drawing Sheets

Latin name of the genus and species: *Rosa hybrida.*
Variety denomination: 'RUIRD0037A'.

BACKGROUND OF THE INVENTION

The new *Rosa* cultivar is a product of a planned breeding program conducted by the inventor. The objective of the breeding program was to produce improved rose varieties. The cross resulting in this new variety was made during Spring of 2003, by the inventor at a research nursery in Hazerswoude, The Netherlands.

The seed parent is the unpatented variety *Rosa* 'DELdog'. The pollen parent is the unpatented *Rosa* 'TANanaistrua'. The new variety was selected in June 2004 by the inventor at the same research nursery in Hazerswoude, The Netherlands. The inventor continued observing characteristics of the new variety for several years, in the controlled conditions of the research nursery.

Asexual reproduction of the new cultivar was performed by vegetative softwood cuttings. This was first performed at a greenhouse in Hazerswoude, The Netherlands, in August 2004, and has shown that the unique features of this cultivar are stable and reproduced true to type in successive generations.

SUMMARY OF THE INVENTION

The cultivar 'RUIRD0037A' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RUIRD0037A' These characteristics in combination distinguish 'RUIRD0037A' as a new and distinct *Rosa* cultivar:

1. Good fragrance.
2. Large yellow flowers.

PARENTAL COMPARISON

Plants of the new cultivar 'RUIRD0037A' are similar to plants of the seed parent, in most horticultural characteristics, however, plants of the new cultivar 'RUIRD0037A' differ in the following:

1. The new variety has darker yellow flowers, while the seed parent has lighter yellow flowers.

Plants of the new cultivar 'RUIRD0037A' are similar to plants of the pollen parent in most horticultural characteristics, however, plants of the new cultivar 'RUIRD0037A' differs in the following;

1. The new variety has yellow flowers, while the pollen parent has red flowers.

COMMERCIAL COMPARISON

Plants of the new cultivar 'RUIRD0037A' can be compared to the commercial variety *Rosa* 'Chewhocan', U.S. Plant Pat. No. 26,914. These varieties are similar in most horticultural characteristics, however 'RUIRD0037A' differs in the following:

1. This new cultivar has single flowers; this comparator has double flowers.
2. Anthers and pollen of new variety are more orange; comparator has lighter yellow anthers and pollen.
3. The new variety has larger flowers than this comparator.

BRIEF DESCRIPTION OF THE PHOTOGRAPHS

Figure 1:
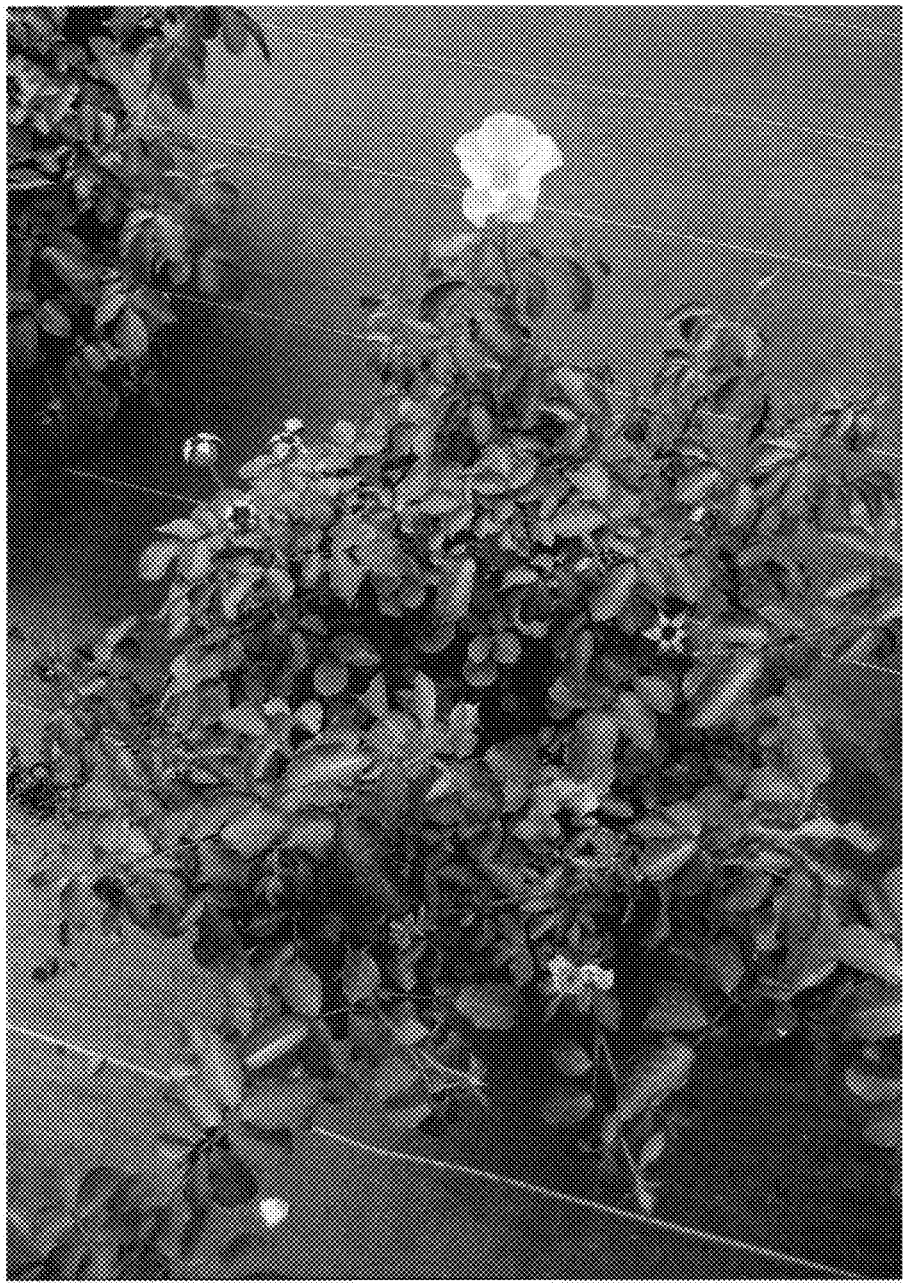

The accompanying photograph in FIG. 1 illustrates in full color a typical plant of 'RUIRD0037A' in a 2 gallon con tainer grown in Grand Haven, Mich. in a polyhouse. Plants in FIG. 1 are approximately 2 to 3 years old.

Figure 2:
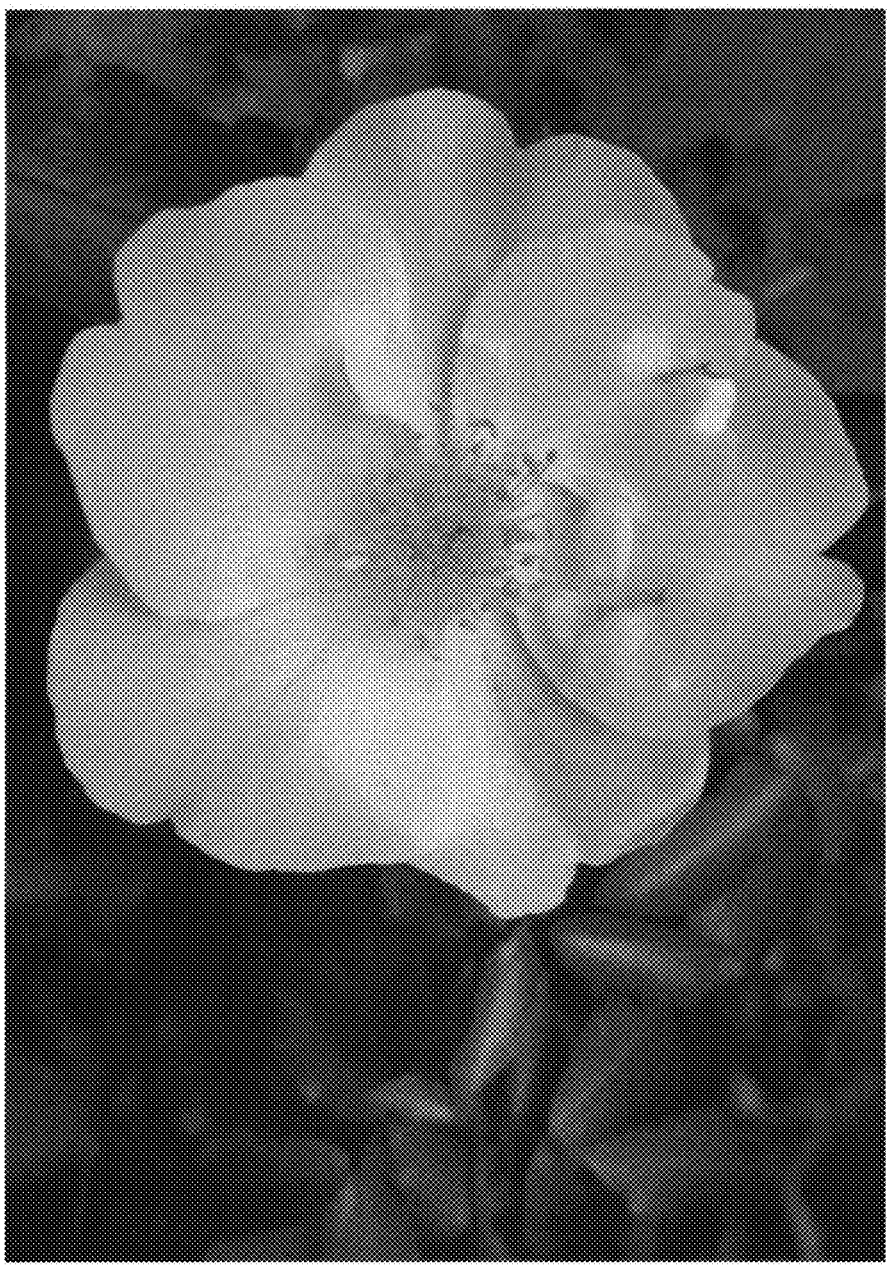

FIG. 2 illustrates a close up view of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'RUIRD0037A' plants grown outdoors, in Hazerswoude, the Netherlands. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'RUIRD0037A'.

Market classification: Floribunda garden rose.

PROPAGATION

Time to initiate roots: 30 days at approximately 20° C.

Time to produce a rooted cutting: 120 days at approximately 20° C.

Root description: Fibrous and fleshy, medium thickness, moderately branched, dense. White in color, not accurately measured with R.H.S. chart.

PLANT

Age of plant described: 2-3 years.

Growth habit: Upright.

Container size: 1, 2, 3, 5 gallon pots.

Height: 67 cm.

Plant spread: 80 cm.

Rootstock: Own root.

Growth rate: Moderate.

Branching habit: Mostly horizontally outwards, arching.

Length of primary lateral branches: 27 cm.

Diameter of lateral branches: 4 mm.

Quantity lateral branches: 10.

Internode length: 2-4 cm.

Stem:

*Appearance*.—Upright.
*Aspect*.—45-90 degrees.
*Strength*.—Strong.
*Color*.—RHS Yellow-Green 146C.
*Pubescence*.—None.

Thorns:

*Number per linear centimeter*.—2.
*Shape*.—Narrow deltoid, bent downward.
*Apex*.—Acuminate.
*Height*.—5 mm.
*Color*.—Immature: RHS Greyed-Red 180A. Mature: RHS Greyed-Red 181A.

FOLIAGE

Leaf:

*Arrangement*.—Alternate.
*Quantity*.—Average 9 per lateral branch.
*Average length*.—5-12 cm.
*Average width*.—8-9 cm.

Leaflet:

*Quantity*.—5 to 7 per leaf.
*Terminal length*.—5.75 cm.
*Terminal width*.—2.75 cm.
*Lateral length*.—4 cm.
*Lateral width*.—2.5 cm.
*Shape*.—Elliptic.
*Apex*.—Acute.
*Base*.—Attenuate.
*Margin*.—Serrate.
*Pubescence*.—None.
*Texture*.—Smooth, glossy.
*Color*.—Young foliage upper side: RHS Green 138A. Young foliage under side: RHS Greyed-Red 181B. Mature foliage upper side: RHS Green 139A. Mature foliage under side: RHS Yellow Green 146B flushed Greyed-Red 181B.
*Venation*.—Pattern: Pinnate. Color, upper side.. RHS Greyed-Orange 163B. Color, mature, under side: RHS Greyed-Orange 167C. Color, immature, under side: RHS Greyed-Red 181C.

Petiole:

*Leaf petiole length*.—2 cm.
*Leaf petiole diameter*.—3 mm.
*Leaflet petiole length*.—2 mm.
*Leaflet petiole diameter*.—1 mm.
*Leaf petiole texture*.—Micro-thorns.
*Leaflet petiole texture*.—Smooth, waxy.
*Leaf petiole color, upper surface*.—RHS Greyed-Red 179C.
*Leaf petiole color, lower surface*.—RHS Yellow-Green 144B.
*Leaflet petiole color, upper surface*.—RHS Yellow-Green 144C flushed Greyed-Red 179A.
*Leaflet petiole color, lower surface*.—RHS Greyed-Red 179C.

Stipule:

*Quantity*.—2.
*Shape*.—Falcate.
*Apex*.—Acuminate.
*Base*.—Truncate.
*Margin*.—Fused with petiole, ciliate.
*Length*.—1-2 cm.
*Width*.—4 cm.
*Texture, upper surface*.—Smooth.
*Texture, lower surface*.—Smooth.
*Color, upper surface*.—RHS Green 137D.
*Color, lower surface*.—RHS Green 137D.

FLOWER

Natural flowering season: Summer.

Flower type and habit: Single rotate.

Quantity of flowers: 1 to 5 per spray.

Sprays per lateral stem: 1.

Flower:

*Shape*.—Round whorl.
*Diameter*.—7 cm.
*Height*.—3 cm.
*Aspect*.—Outward or upward facing.
*Persistent or self-cleaning*.—Persistent.
*Fragrance*.—Sweet.

Peduncle:

*Length*.—6 cm.
*Diameter*.—2 mm.
*Angle*.—Upright, straight.

*Strength*.—Strong.
*Texture*.—Prickly.
*Color*.—RHS Green 143B.

Petals:
*Arrangement*.—Whorled.
*Appearance*.—Intense, deeply pigmented.
*Petal quantity*.—Average 8.5.
*Fused*.—No.
*Length*.—3 cm.
*Width*.—2.5-3.5 cm.
*Shape*.—Obovate.
*Margin*.—Entire.
*Apex*.—Obocordate.
*Base*.—Obtuse.
*Texture*.—Smooth, silky.
*Color*.—When opening: Upper surface: RHS Yellow-Orange 17C. Lower surface: RHS Yellow-Orange 17C. Fully opened: Upper surface: RHS Yellow 7D. Lower surface: RHS Yellow 7D.

Petaloids: None.

Bud:
*Shape*.—Ovate.
*Length*.—2 cm.
*Diameter*.—1 cm.
*Color*.—RHS Green 143B.

Sepals:
*Quantity*.—5.
*Arrangement*.—Whorled.
*Length*.—1.75 cm.
*Width*.—1 cm.
*Shape*.—Acuminate.
*Apex*.—Acuminate.
*Base*.—Truncate.
*Margin*.—Pubescent.
*Color*.—Immature, Upper Side: RHS Green 142D. Immature, Under Side: RHS Green 143B. Mature, Upper Side: RHS Green 142D. Mature, Under Side: RHS Green 143B.
*Texture*.—Upper: Pubescent. Lower: Smooth with bumps.

Peduncle:
*Length*.—6 cm.
*Diameter*.—2 mm.
*Angle*.—Upright.
*Strength*.—Strong.
*Texture*.—Prickly.
*Color*.—RHS Green 143B.

Receptacle:
*Length*.—1 cm.
*Width*.—1.2 cm.
*Shape*.—Obovate.
*Texture*.—Smooth.
*Color*.—RHS Green 143B.

REPRODUCTIVE ORGANS

Stamens:
*Quantity*.—Average 100.
*Filament length*.—Average 1 cm.
*Filament color*.—RHS Yellow 6A.

Anthers:
*Length*.—2 mm.
*Shape*.—Club-like.
*Color*.—RHS Yellow-Orange 22A.
*Pollen*.—Color: RHS Yellow-Orange 22A. Quantity: Moderate.

Pistil:
*Number*.—50.
*Length*.—4 mm.

Stigma:
*Shape*.—Diffuse.
*Color*.—RHS Greyed-Orange N167C.

Style:
*Length*.—5 mm.
*Color*.—RHS Greyed-Yellow 160B.

OTHER CHARACTERISTICS

Seeds and fruits: Not observed.

Disease/pest resistance: Good overall disease resistance to normal pests and diseases typical of garden roses. Very good resistance to blackspot diseases.

What is claimed is:

1. A new and distinct hybrid cultivar of *Rosa* plant named 'RUIRD0037A' as herein illustrated and described.

* * * * *